(12) United States Patent
Piotrowski et al.

(10) Patent No.: US 9,585,554 B2
(45) Date of Patent: Mar. 7, 2017

(54) IMAGE PROCESSING APPARATUS AND IMAGE PROCESSING METHOD

(71) Applicant: CANON KABUSHIKI KAISHA, Tokyo (JP)

(72) Inventors: Krzysztof Marek Piotrowski, Wroclaw (PL); Yukio Sakagawa, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 674 days.

(21) Appl. No.: 13/962,115

(22) Filed: Aug. 8, 2013

(65) Prior Publication Data

US 2014/0063447 A1 Mar. 6, 2014

(30) Foreign Application Priority Data

Aug. 30, 2012 (JP) ................. 2012-190610

(51) Int. Cl.
*A61B 3/14* (2006.01)
*A61B 3/10* (2006.01)
*A61B 3/00* (2006.01)

(52) U.S. Cl.
CPC .................. *A61B 3/102* (2013.01)

(58) Field of Classification Search
CPC A61B 3/14; A61B 3/103; A61B 3/113; A61B 3/1225; A61B 3/024; A61B 3/032; A61B 3/1015
USPC ........ 351/206, 200, 205, 209–210, 221–223, 351/246
See application file for complete search history.

(56) References Cited

U.S. PATENT DOCUMENTS

| 2012/0050282 A1* | 3/2012 | Sakagawa | A61B 3/0025 345/419 |
| 2012/0063660 A1* | 3/2012 | Imamura | A61B 5/0066 382/131 |
| 2013/0194544 A1* | 8/2013 | Iwase | A61B 3/102 351/206 |
| 2013/0195340 A1* | 8/2013 | Iwase | G06K 9/00617 382/131 |

FOREIGN PATENT DOCUMENTS

| JP | 2008-073099 A | 4/2008 |
| JP | 2008-295804 A | 12/2008 |
| JP | 2011-024930 A | 2/2011 |
| JP | 2012-020061 A | 2/2012 |
| WO | 2012/018303 A1 | 2/2012 |

* cited by examiner

*Primary Examiner* — Dawayne A Pinkney
(74) *Attorney, Agent, or Firm* — Carter, DeLuca, Farrell & Schmidt, LLP

(57) ABSTRACT

There is provided an image processing apparatus, comprising: a tomographic image acquiring unit for acquiring a tomographic image of a retina; an instruction unit for instructing for a change in the positions of display forms indicating a plurality of regions in one of the display forms indicating a plurality of layer boundaries of a retina; and a display control unit for causing the display unit to display respective display forms indicating the plurality of layer boundaries in positions corresponding to the plurality of layer boundaries in the tomographic image in an overlapped state, and in a case of instructing for the change in the position of at least one of display forms, for causing the display unit to display the display form instructed with the display form different from other display forms.

15 Claims, 5 Drawing Sheets

IMAGE PROCESSING APPARATUS AND IMAGE PROCESSING METHOD

BACKGROUND OF THE INVENTION

Field of the Invention

The present invention relates to an image processing apparatus and an image processing method for processing an image.

Description of the Related Art

A technology for an optical coherence tomography (OCT) apparatus is applied to the medical field. An ophthalmic tomographic image photographing apparatus enables three-dimensional observation of an internal state of a retina layer. This tomographic image photographing apparatus has become popular for its capability of more appropriately diagnosing diseases.

Japanese Patent Application Laid-Open No. 2008-073099 discloses a technology of obtaining a position of a layer boundary by sequentially referring to pixel values of a tomographic image along a depth direction of a fundus in a conventional technology for retinal layer analysis. An ophthalmological diagnosis, which necessitates grasping in units of layers that form a retina, involves displaying of a form and a thickness of each layer on the tomographic image of the retina or three-dimensional displaying in units of layers.

Here, an examiner sometimes wishes to correct a position of a layer boundary of a retina by an editing operation. Further, in recent years, the number of layers in demand has been increasing more than before owing to an increase in image quality of a tomographic image, an improvement in analysis accuracy, and the like. At this time, if the number of layer boundaries of the retina in the tomographic image increases, the editing operation for positions thereof becomes complicated.

SUMMARY OF THE INVENTION

In view of the above-mentioned problem, one of objects of the present invention is to allow an examiner to perform an editing operation for layer boundaries of a retina in a tomographic image with ease.

There is provided an image processing apparatus, comprising: a tomographic image acquiring unit for acquiring a tomographic image of a retina, an instruction unit for instructing for a change in the positions of display forms indicating a plurality of regions in one of the display forms indicating a plurality of layer boundaries of a retina, a display control unit for causing the display unit to display respective display forms indicating the plurality of layer boundaries in positions corresponding to the plurality of layer boundaries in the tomographic image in an overlapped state, and in a case of instructing for the change in the position of at least one of display forms, for causing the display unit to display the display form instructed with the display form different from other display forms; and a layer boundary information changing unit for changing information on the position of the layer boundary based on the change of the position of the display form instructed by the instruction unit.

According to the present invention, the examiner is allowed to perform the editing operation for the layer boundaries of the retina in the tomographic image with ease.

Further features of the present invention will become apparent from the following description of exemplary embodiments with reference to the attached drawings.

DESCRIPTION OF THE EMBODIMENTS

In the following, embodiments of the present invention are described with reference to the accompanying drawings.

First embodiment: update information on layer boundary based on change in position of layer boundary In the following, a first embodiment of the present invention is described with reference to the accompanying drawings. An image processing apparatus according to this embodiment first causes display means to display a display form indicating a layer boundary with an overlap in a position corresponding to the layer boundary in the tomographic image of the retina displayed on the display means in response to an instruction issued by an examiner (operator) through instruction means. Here, examples of the display form indicating the layer boundary include a line indicating the layer boundary. At this time, it is possible to edit at least one point among a plurality of points being an example of display forms indicating a plurality of regions on the line indicating the layer boundary. For example, the examiner can change the position of this point to thereby change the position of the line indicating the layer boundary with ease. Further, based on the change of this point, it is also possible to automatically update the position of an adjacent point and the position of the line indicating another layer boundary. Note that, the display form indicating the layer boundary may be a dotted line or a bold line instead of the line. Further, the display form indicating the plurality of regions may be a shape such as a quadrangle or a star shape instead of the point.

Figure 1:
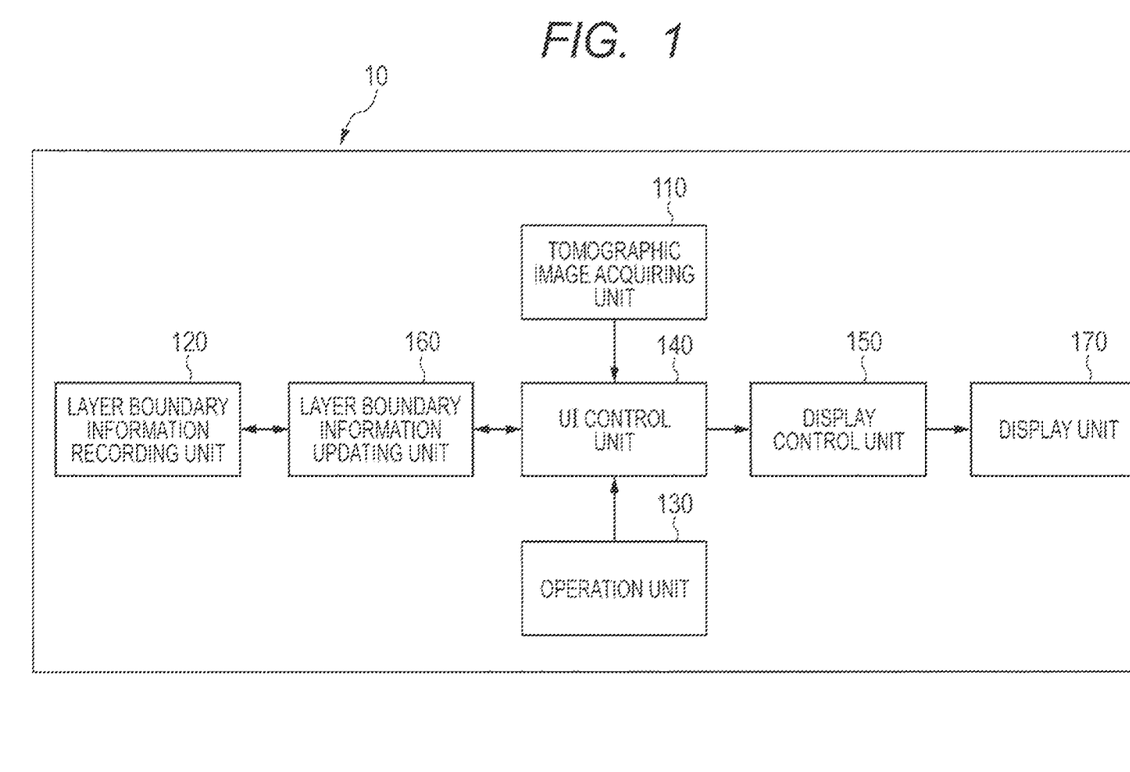
FIG. 1 is a block diagram illustrating a functional configuration of an image processing apparatus according to a first embodiment.

First, FIG. 1 is a block diagram illustrating a functional configuration of an image processing apparatus 10. The image processing apparatus 10 includes a tomographic image acquiring unit 110, a layer boundary information recording unit 120, an operation unit 130, a UI control unit 140, a display control unit 150, a layer boundary information updating unit 160, and a display unit 170.

The tomographic image acquiring unit 110 being tomographic image acquiring means acquires a tomographic image from a data server (not shown) for recording a tomographic image picked up in advance, for example, a tomographic image of a retina. Alternatively, the tomographic image acquiring unit 110 sends an image pick-up command to a tomographic image pick-up apparatus (not shown), and acquires the picked-up tomographic image.

The tomographic image pick-up apparatus according to this embodiment is an apparatus that enables a measuring light being low-coherence light to be applied to a sample and backward scattered light from the sample to be measured by using an interference system. When the measuring light is applied to one point on the sample, it is possible to obtain image information along a depth direction in the one point on the sample. In addition, by performing measurement while scanning the measuring light on the sample, it is also possible to obtain a section image of the sample.

Then, in a case of being applied to a fundus, the tomographic image pick-up apparatus can pick up the tomographic image of the fundus of an eye to be inspected with a high resolution by scanning the measuring light on the fundus of the eye to be inspected. An optical coherence tomographic imaging apparatus generally employs a photographing method of obtaining a plurality of tomographic images by repeatedly scanning the fundus to be measured in a horizontal direction or a vertical direction. For example, it is also possible to obtain a three-dimensional image of the fundus while repeating a scan a plurality of times by shifting a scan position in parallel. One vertical line of the tomographic image is called "A-scan". If an image pick-up position of the tomographic image on the retina can be identified, it is also possible to identify the position of the A-scan on the retina. Alternatively, it is also possible to identify relative photographing positions between the A-scans.

Figure 4A:
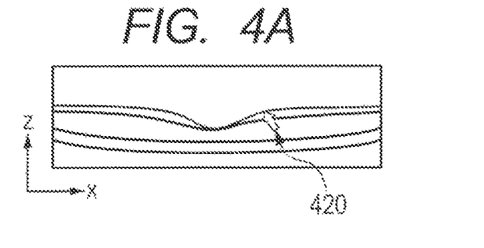
FIGS. 4A, 4B, 4C, 4D, 4E, 4F, 4G and 4H are diagrams illustrating processing results according to the example of the embodiment of the present invention.
Figure 4B:
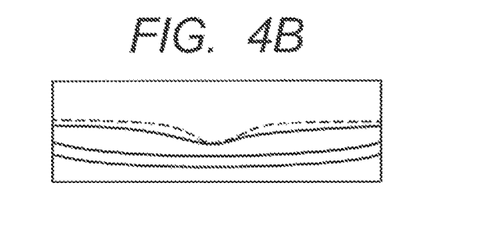
Figure 4C:
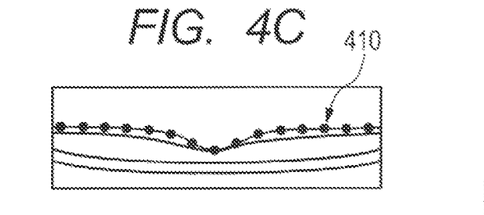
Figure 4D:
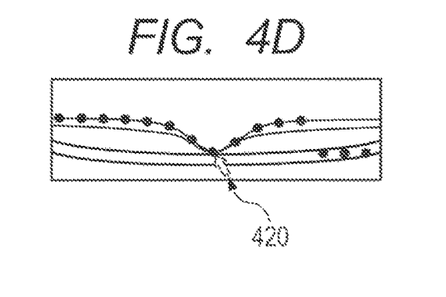

FIG. 4A illustrates an example of the tomographic image displayed on the display unit 170. In FIG. 4A, one tomographic image is a 2-D image, and a coordinate system within FIG. 4A represents a coordinate system of the tomographic image. An origin point of the coordinate system of the tomographic image is assumed to be located at the bottom left of the image. Then, positional information of (X,Z) is given to each pixel of the tomographic image. If the position of the tomographic image itself can be identified, it is also possible to identify positional information of (X,Y,Z) for the pixel. FIG. 4G illustrates an example of a tomographic image group (3-D tomographic image) photographed in a 3-D manner.

The layer boundary information recording unit 120 being an example of layer boundary information recording means previously analyzes the tomographic image acquired from the tomographic image acquiring unit 110, and records a result of calculating the positional information on the layer boundary. Alternatively, the operator records a result of editing the positional information on the layer boundary. In this embodiment, not only a retina layer and a layer boundary line but also a membrane is a subject as the layer boundary line in the tomographic image of the retina. Specifically, there are ILM, NFL/GCL, GCL/IPL, IPL/INL, INL/OPL, OPL/ONL, IS/OS, OS/RPE, RPE/Choroid, and BM. A list of the layer boundaries such as aforementioned are displayed on display unit 170 through the display control unit 150 in an aspect as shown in FIG. 4F. Actually, the layer boundaries which have been processed or were processed are displayed with so-called check mark. However, this proposition is not limited to those layer boundary lines, and boundaries, membranes, structures, and the like of anatomical regions other than the retina may be used.

In response to an operation performed by the operator, the operation unit 130 outputs an operation signal indicating an editing operation for the position of the layer boundary to the UI control unit 140. As the operation unit 130, different kinds of device such as a mouse, a trackball, and a joystick for moving a cursor on a GUI may be used. For example, consideration is given to a case where the operation unit 130 is a mouse provided with a button and a scroll wheel. The operation unit 130 receives a temporary press-down operation (click) on the button against the operation unit 130, and outputs an operation signal indicating that the click has been performed to the UI control unit 140. Further, for example, when the scroll wheel of the operation unit 130 being the mouse is rotated, the operation unit 130 outputs an operation signal indicating a rotation amount of the scroll wheel and an operation signal indicating a rotation direction of the scroll wheel to the UI control unit 140. In addition, for example, when the operation unit 130 being the mouse moves, the operation unit 130 outputs an operation signal indicating a movement of the operation unit 130 to the UI control unit 140.

For example, the UI control unit 140 causes the display control unit 150 to display different kinds of image based on the signals output from the tomographic image acquiring unit 110, the layer boundary information recording unit 120, and the operation unit 130. For example, the UI control unit 140 is realized by a processing device such as a central processing unit (CPU) executing a program recorded in a memory (not shown).

For example, the UI control unit 140 causes the display control unit (display control means) 150 to display an index that moves in accordance with an instruction of the operation unit 130 and that indicates an arbitrary position on the display unit (display means) 170 formed of a monitor (not shown) or the like. For example, a cursor having an arrow shape can be used as this index, but the present invention is not limited thereto, and any index that can indicate an arbitrary position on the display unit 170 may be used.

In addition, the UI control unit 140 can recognize coordinates on the display unit 170, and can recognize through the display control unit 150 which region on the display unit 170 the index falls within based on the operation signal input from the operation unit 130. Further, the UI control unit 140 can recognize the coordinates of the region on the display unit 170 in which the tomographic image is displayed. Accordingly, for example, if the operation unit 130 is the mouse, based on the operation signal indicating the movement of the mouse, it is possible to recognize the position on the display unit 170 of the index that moves so as to correspond to the movement of the mouse. In addition, it is possible to recognize whether or not the index that moves so as to correspond to the operation of the operation unit 130 falls within the region on the display unit 170 in which the tomographic image is displayed.

Further, in a case where the index is located on the tomographic image, for example, each time the scroll wheel is rotated, the UI control unit 140 displays the next tomographic image. Alternatively, the layer boundary line that is closest to the index can be selected by a mouse click operation. Alternatively, a change amount by which the position of the layer boundary in the tomographic image is changed based on the operation signal input from the operation unit 130 is calculated. Note that, the unit of the change amount calculated by the UI control unit 140 is, for example, the pixel. More specifically, for example, in the case where the operation unit 130 is the mouse, when a click is performed on the tomographic image with the index located on the tomographic image, the UI control unit 140 receives the operation signal corresponding to the click. Then, the UI control unit 140 determines the coordinates of the index at a time when the click is performed and a predetermined position of the region in which the tomographic image is displayed on the display unit 170, and selects the layer boundary line that is closest to the index. In order to allow the layer boundary line selected by the operator to be identified with ease, for example, the line indicating the layer boundary may be drawn on the tomographic image. At the time of the drawing, the display form of the layer boundary line is changed. For example, it is preferred that the line indicating the layer boundary be displayed in a color different from the others. Further, the line indicating the layer boundary may be blinked or drawn as a bold line or a dotted line. Alternatively, in a case where the index is moved with the button of the mouse being depressed after the layer boundary line is selected, the UI control unit 140 may be configured to determine a movement amount thereof as the change amount of the position of the layer boundary. The unit of this distance is, for example, the pixel.

Note that, for example, in a case where a keyboard is used as the operation unit 130, the click corresponds to the press-down of an enter key, and the rotation of the scroll wheel may correspond to the press-down of a key for a vertical direction of direction keys. Note that, another key of the keyboard may be assigned with regard to the movement of the index, or the mouse may be used with regard to the movement of the index.

Note that, the UI control unit 140 subjects an anterior ocular segment image to processing such as contrast adjustment, windowing adjustment, or noise filtering of the tomographic image.

The display control unit 150 displays a GUI screen or a tomographic image that is being edited on the display unit 170 under control of the UI control unit 140. In other words, the display control unit 150 functions as an example of a control device for causing the display unit 170 being the display means to display the GUI for editing the tomographic image.

The layer boundary information updating unit 160 being an example of layer boundary information changing means updates (changes) layer boundary information, for example, information on the position of the layer boundary in response to the instruction for the change of the operation unit 130 being an example of the instruction means. For example, the layer boundary information updating unit 160 is realized by the processing device such as a central processing unit (CPU) executing a program recorded in a memory (not shown).

(Operation Flow of Image Processing Apparatus)

Figure 2:
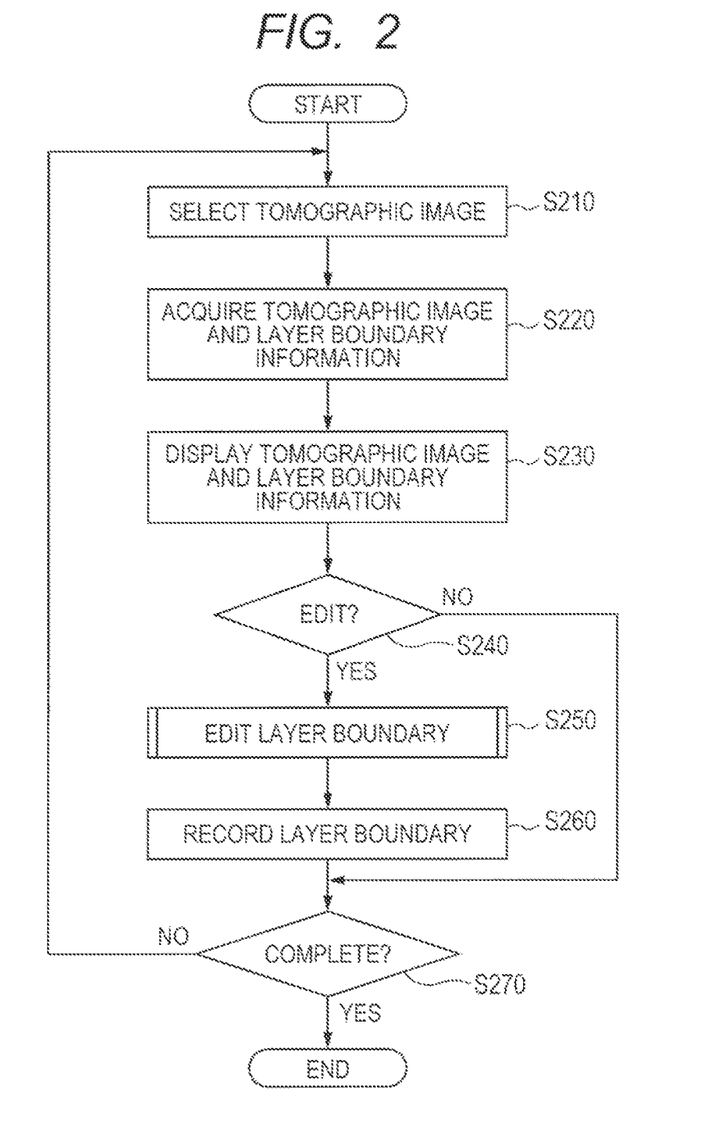
FIG. 2 is a flowchart for illustrating a system operation according to the first embodiment.

Next, an operation of the image processing apparatus 10 serving as an example of the embodiment, which is configured as described above, is described with reference to a flowchart illustrated in FIG. 2.

<Step S210: Select Tomographic Image>

In Step S210, the UI control unit 140 selects the tomographic image to be edited in response to the operation performed by the operator through the operation unit 130. In this embodiment, the UI control unit 140 acquires one tomographic image from the tomographic image acquiring unit 110, and displays the tomographic image on the display unit 170. Here, as an example, the tomographic image being displayed is set as an n-th tomographic image. Then, when the index indicating the position of the mouse of the operation unit 130 is located on the tomographic image, the display is switched to the adjacent tomographic image based on the rotation of a mouse wheel. An (n+1)-th or (n−1)-th tomographic image is displayed based on the rotation direction of the scroll wheel. It should be understood that n represent one of tomographic images obtained by continuous photographing, and that the tomographic image not be switched when (n+1) or (n−1) does not exist. The tomographic image displayed last in Step S210 is the tomographic image to be edited.

Note that, another method of selecting the tomographic image may be employed. For example, the UI control unit 140 may set a number input through the keyboard of the operation unit 130 as a number given to the tomographic image to be edited. Alternatively, a button indicating numbers given to the tomographic images that can be edited may be placed on the GUI of the display unit 170 and may be mouse-clicked in response to the operation of the operation unit 130 to thereby select the corresponding tomographic image.

<Step S220: Acquire Tomographic Image and Layer Boundary Information>

In Step S220, the UI control unit 140 acquires the tomographic image selected in Step S210 from the tomographic image acquiring unit 110, and further acquires the layer boundary information on the selected tomographic image from the layer boundary information recording unit 120. The UI control unit 140 sends the selected tomographic image and the layer boundary information corresponding to the tomographic image to the display control unit 150. Then, based on the layer boundary information, the display control unit 150 causes the display unit 170 to display the layer boundary line being an example of the display form indicating the layer boundary in the position corresponding to the layer boundary line in the tomographic image in an overlapped (composited) state.

<Step S230: Display Tomographic Image and Layer Boundary Information>

In Step S230, based on the tomographic image selected in Step S210 and the information on the layer boundary line of the selected tomographic image which is obtained in Step S220, the UI control unit 140 overlays a line expressing a boundary line on the tomographic image and causes the display control unit 150 to create a composite image. Here, individual boundary lines are drawn in colors different from one another in order to be recognized with ease. For example, the drawing is performed for ILM in yellow, NFL/GCL in green, GCL/IPL in blue, IPL/INL in navy, INL/OPL in purple, OPL/ONL in yellowish green, IS/OS in dark green, OS/RPE in brown, RPE/Choroid in orange, and BM in pink. However, the present invention is not limited to those colors, and a combination of other colors may be employed, or the same color may be given to a plurality of boundary lines. After creating the composite image of the tomographic image and the boundary line, the UI control unit 140 sends the composite image to the display control unit 150, and the display control unit 150 causes the display unit 170 to present the composite image to the operator.

<Step S240: Determine Whether or not to Edit Layer Boundary Information>

In Step S240, the UI control unit 140 determines whether or not the information on the layer boundary line is to be updated (edited) in response to the operation of the operator received from the operation unit 130. In this embodiment, the UI control unit 140 provides an "edit" button to the GUI of the display unit 170, and starts editing when the operator clicks on the edit button by using a mouse cursor. However, it suffices that an intention of the operator can be conveyed, and hence instead of the button on the GUI, for example, a hot key of the keyboard may be used or a specific button may be prepared. When the editing is started, the processing advances to Step S250. When the editing is not performed, the processing advances to Step S270.

<Step S250: Edit Layer Boundary Information>

In Step S250, the UI control unit 140 and the layer boundary information updating unit 160 update (edit) the information on the layer boundary line in response to the operation of the operator. Step S250 is described in detail later.

<Step S260: Record Layer Boundary Information>

In Step S260, the layer boundary information recording unit 120 records the layer boundary information edited in Step S250.

<Step S270: Determine Whether or not to Finish Work>

In Step S270, the UI control unit 140 determines whether or not another tomographic image is to be edited in response to the operation of the operator received from the operation unit 130. In this embodiment, the UI control unit 140 provides a "finish work" button and a "continue work" button to the GUI of the display unit 170. When the operator clicks on the "finish work" button by using the mouse cursor, the processing of the image processing apparatus 10 according to this embodiment is brought to an end. Alternatively, when the operator clicks on the "continue work" button by using the mouse cursor, the processing returns to Step S210. However, instead of this embodiment, for example, "finish work" and "continue work" may be assigned to hot keys of the keyboard. Alternatively, for example, the operation unit 130 may detect that a different tomographic image has been selected.

(Editing Flow for Layer Boundary Information)

Figure 3A:
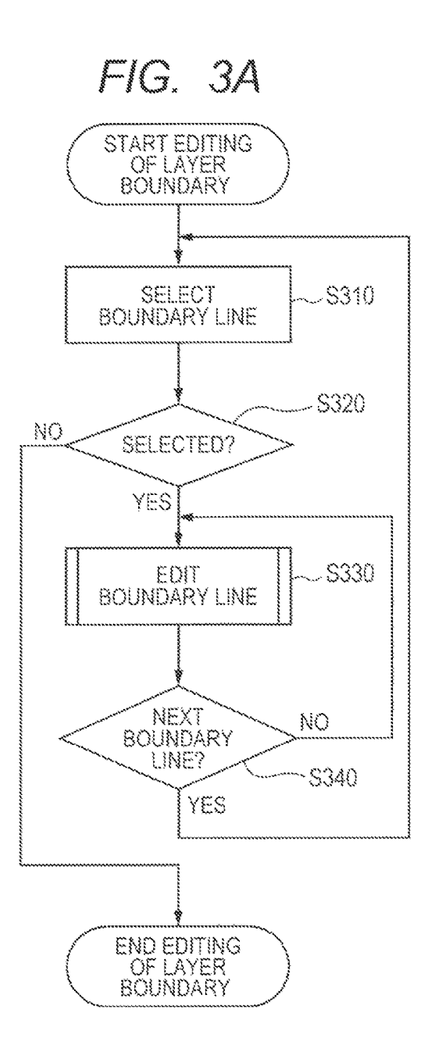
FIGS. 3A and 3B are flowcharts for illustrating a system operation in detail according to an example of an embodiment of the present invention.

Next, the processing of Step S250 is described in detail with reference to a flowchart of FIG. 3A.

<Step S310: Select Boundary Line>

In Step S310, the UI control unit 140 selects the boundary line to be edited in response to the operation of the operator received from the operation unit 130. In this embodiment, the composite image of the tomographic image and the information on the boundary line, which is displayed by the display control unit 150 in Step S230, is used. When the operator performs a mouse-click on the composite image while holding the mouse cursor on the boundary line, the operation unit 130 acquires the position of the mouse-click on the composite image. Then, the UI control unit 140 can select, through the display control unit 150, the boundary line that is closest to the position that has been mouse-clicked on the composite image. In addition, it is preferred that the selected boundary line be changed to, for example, highlight display in a case of being selected. In this embodiment, a state in which the boundary line is selected is expressed by the dotted line. FIG. 4A illustrates an example of the operation. Reference numeral 420 indicates an example in which, when the mouse-click is detected in the position of the mouse cursor, the selected boundary line becomes the dotted line in FIG. 4B.

In this embodiment, a method of directly selecting the boundary line by identifying the position of the mouse-click has been described, but the present invention is not limited to this method, and another method of selecting the boundary line may be employed. For example, as illustrated in FIG. 4F, it is also possible to list names of boundary lines that can be selected and to allow the boundary line to be selected by using the mouse or the hot key (function assigned to a key of the keyboard).

In this embodiment, the layer boundary information updating unit 160 sets (arranges) control points in a portion of the tomographic image corresponding to the line indicating the selected boundary line (region corresponding to the selected boundary line). Those control points are displayed on the display unit 170 as input points for inputting the operation of the operator, and are arranged on the layer boundary line by a module area that functions as operation input means in the layer boundary information updating unit 160 along with the operation unit 130 used to execute Step S331 described later. In addition, the display control unit 150 performs the display by overlaying the selected boundary line on the tomographic image being displayed, and displays the control points thereon. FIG. 4C illustrates an example of the display. In this embodiment, 50 control points are arranged on the boundary line at regular intervals. It should be understood that the present invention not be limited to this arrangement, and the number of control points may be changed depending on a length of the boundary line, or the shape of the boundary line may be analyzed to arrange the control points closely to each other on a side exhibiting more changes and to reduce the control points for a smooth part of the boundary line. Alternatively, another arrangement method may be employed.

In addition, in this embodiment, a "finish editing" button is provided to the GUI of the display unit 170, and the operator is allowed to select the boundary line to be edited or to click on the finish editing button.

<Step S320: Determine Whether or not Boundary Line has been Selected>

In Step S320, the UI control unit 140 determines whether or not the boundary line has been selected. When it is detected in Step S310 that the "finish editing" button has been clicked on, the UI control unit 140 judges that the boundary line has not been selected, and the processing of Step S250 is brought to an end.

When the boundary line is selected in Step S310, the processing advances to Step S330.

<Step S330: Edit Boundary Line>

In Step S330, the layer boundary information updating unit 160 updates the information on the selected boundary line based on the information of the operation unit 130 and the UI control unit 140. Details of operations in Step 330 are described below.

<Step S340: Determine Whether or not to Edit Another Boundary Line>

In Step S340, the UI control unit 140 determines whether or not another boundary line is to be edited in response to the operation of the operator received from the operation unit 130. In this embodiment, the UI control unit 140 provides a "reselect boundary line" button to the GUI of the display unit 170. When the operator uses the mouse cursor to click on the "reselect boundary line" button, the UI control unit 140 detects the operation, and the processing returns to Step S310. Alternatively, when the UI control unit 140 does not have the "reselect boundary line" button clicked on, the processing returns to Step S330.

(Editing Flow for Boundary Line)

Figure 3B:
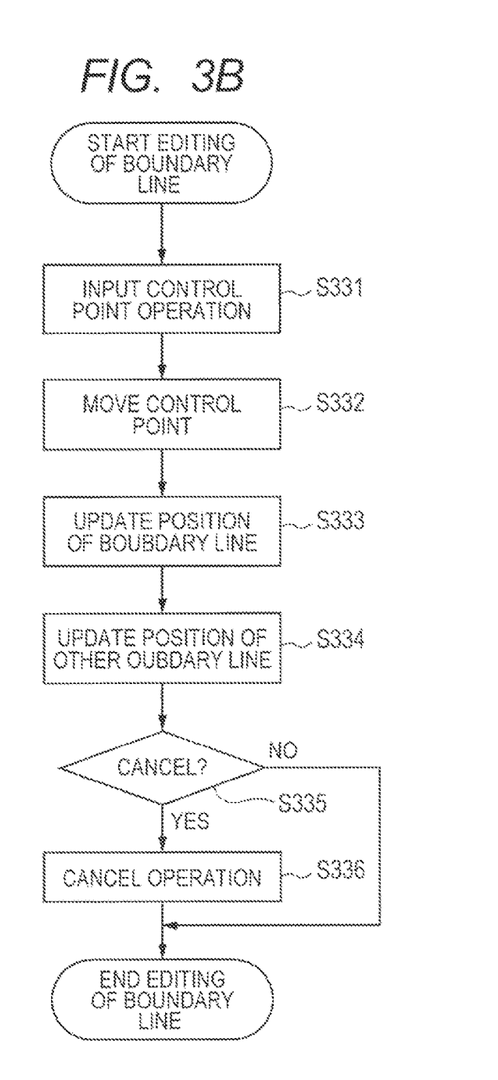

Next, the processing of Step S330 is described in detail with reference to a flowchart of FIG. 3B.

<Step S331: Input Operation for Control Point>

In Step S331, the UI control unit 140 displays a control point 410 on the boundary line to be edited, and inputs the operation of the operator received from the operation unit 130. In this embodiment, the composite image of the tomographic image and the boundary line to be edited, which are displayed by the display control unit 150 in Step S310, and the control points on the boundary line is used.

In this embodiment, the position of the control point is changed, to thereby change the position of the boundary line. When the operator performs a mouse-click on the composite image while holding the mouse cursor on the control point, the operation unit 130 acquires the position of the mouse-click on the composite image. Then, the UI control unit 140 can select the control point that is closest to the position that has been mouse-clicked on the composite image.

In addition, the control point is set on the same boundary line in the tomographic image that is not being displayed.

<Step S332: Move Control Point>

In Step S332, the layer boundary information updating unit 160 moves the selected control point. When the operator moves the mouse cursor with a click (long press) on the mouse, the UI control unit 140 receives information on the movement of the cursor from the operation unit 130 and sends the information to the layer boundary information updating unit 160, and the layer boundary information updating unit 160 updates the position of the selected control point based on the movement of the cursor. The layer boundary information updating unit 160 functions as the layer boundary information changing means for updating the information on the layer boundary line through the control point being the input point. In this embodiment, the selected control point displayed by the display control unit 150 moves to the same point as the mouse cursor. Note that, the description is made on the assumption that the position of the boundary line is updated after the click (long press) on the mouse is released, but the present invention is not limited thereto, and it is also conceivable that the boundary line is updated even during the long press. Here, with the X- and Y-positions fixed, the control point moves in a depth direction of the tomographic image, in other words, a Z-direction. However, in the same idea, the control point may move along any axis.

<Step S333: Update Position of Boundary Line>

In Step S333, the layer boundary information updating unit 160 recalculates the position of the layer boundary line based on the control point moved in Step S332. In this embodiment, first, the position of the layer boundary line displayed in the tomographic image is recalculated. It is preferred that the layer boundary information changing means perform, based on the changed position, interpolation for the position of a region other than the plurality of regions in display forms indicating a plurality of layer boundaries. This allows, for example, the position between the control points to be changed so as to smoothly connect between the control points in the layer boundary line based on the position of the control point. Therefore, it is possible to display a smooth layer boundary line.

Specifically, based on the control point on the layer boundary line, the interpolation is performed for the position of the layer boundary line between the control points. In this embodiment, Akima interpolation is performed as an interpolation algorithm. However, this embodiment is not limited to the interpolation algorithm, and any interpolation algorithm such as spline interpolation may be used as long as the position of the layer boundary line between the control points can be interpolated. Here, the interpolation is performed for a Z-direction position of the boundary line located in the position (x,y). In other words, $$Pz(x,y)=Int(x,y) \quad (1)$$

where Pz represents the position in the depth direction (Z-direction) of the boundary line located in the (x,y) position and Int(x,y) represents the interpolation.

In addition, when recalculation of the position of the layer boundary line in the tomographic image being edited is finished, the control points in the tomographic image whose positions are adjacent thereto on the retina are used to perform layer boundary line interpolation between the tomographic images as well. In this embodiment, calculation is performed by creating a one-dimensional list of the control points, but it is also conceivable that 2-D grid control points are used to perform the calculation for the interpolation.

In addition, the position of the control point can be assumed as a pixel position on the image, but in this embodiment, for the calculation for the interpolation, the position of the control point is calculated as the position on the retina (in units of micrometers). In the same manner, the position of the control point in the adjacent tomographic image is assumed as the position on the retina.

In addition, for the sake of the interpolation, instead of inputting all the control points as samples for the interpolation, the control points may be reduced to half or ⅓ samples or may be thinned out to a further degree. It may be assumed that the control points in the adjacent tomographic image are thinned out in the same manner. With such processing, the positions of the control points in the adjacent tomographic image are also subjects to be interpolated. By performing the interpolation, it is possible to smooth out the position of the adjacent layer boundary line.

(Change Position of Layer Boundary Line of Adjacent Tomographic Image Based on Change of Position of Layer Boundary Line)

Figure 4E:
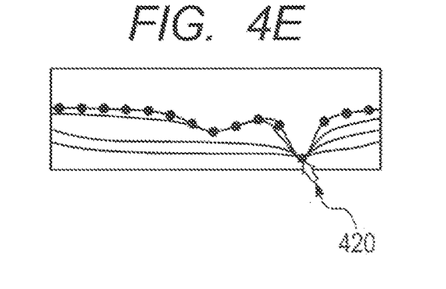
Figure 4F:
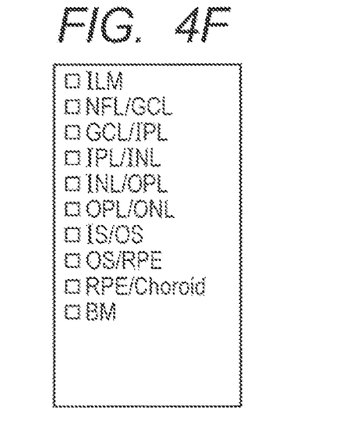
Figure 4G:
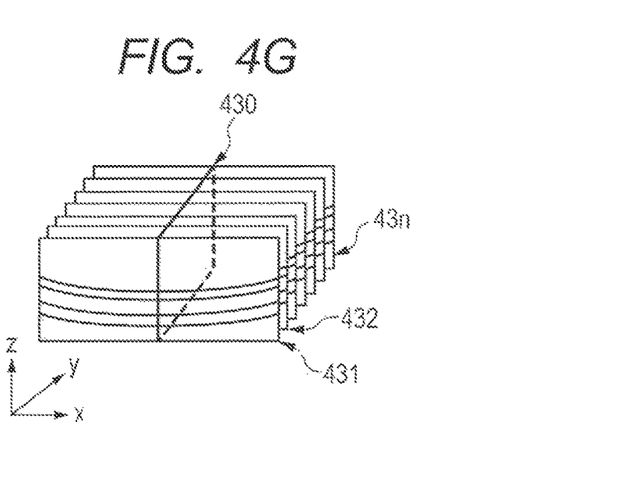
Figure 4H:
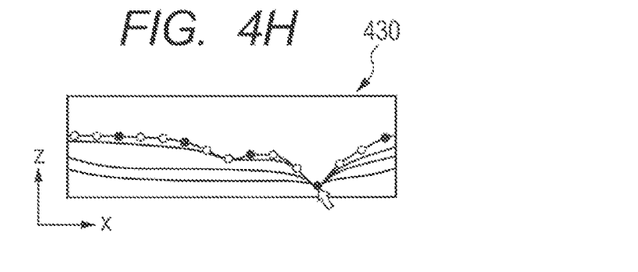

FIGS. 4E, 4G, and 4H illustrate processing results of Step S333.

FIG. 4G illustrates an example of correcting the layer boundary line in the adjacent tomographic image. Reference numerals 431, 432, and 43n are examples of tomographic images of a 3-D tomographic image. Reference numeral 430 represents the tomographic image reconstructed from the plurality of tomographic images. FIG. 4H illustrates the tomographic image 430. In FIG. 4H, the plurality of control points are illustrated in the layer boundary line. The respective control points are formed of information on the different tomographic images of FIG. 4G. In FIG. 4H, the cursor 420 indicates the movement of the control point. The black circles are used to input the samples for the interpolation. The white circles are examples of the control points to be moved based on calculation results of the interpolation. As described above, the layer boundary line in the position in which the input points other than the input point obtained by inputting the operation are arranged is subjected to the interpolation by the layer boundary line changing means.

Step S334: Update Position of Another Boundary Line>

In Step S334, the layer boundary information updating unit 160 calculates the position of another boundary line. In the retina, the adjacent layer boundaries do not intersect each other anatomically. Therefore, it is preferred that this embodiment be configured to inhibit an order of the display forms indicating the layer boundaries in the Z-direction from being changed. Specifically, processing is performed so that the lines indicating the adjacent layer boundaries may not intersect (that the line indicating one layer boundary may not exceed the line indicating another layer boundary in terms of the depth direction of the retina). This processing is executed by the layer boundary information updating unit 160 for changing the information on the layer boundary line regarding another layer other than the layer composited with the layer boundary line based on the change in the information on the layer boundary line on which the input points are arranged in the tomographic image, and in changing of the information on another layer boundary line, the information on that layer boundary line is changed so as to inhibit the layer boundary lines from intersecting. When the layer boundary line including the control point moved in Step S333 is brought into contact with another layer boundary line (for example, layer boundary line B), if an attempt is made to move the control point farther to a layer boundary line B side, it is preferred that the layer boundary information updating unit 160 change the position of the layer boundary line B in accordance with the movement of the control point. Alternatively, the position of the layer boundary line B may be fixed so as to inhibit the control point from moving across the layer boundary line B. At this time, it suffices to maintain a positional relationship between the lines indicating a plurality of layer boundaries along the depth direction of the retina. Note that, in this specification, it is assumed that the above-mentioned positional relationship is maintained even when the lines indicating two layer boundaries are brought into contact with each other with an overlap in the same portion.

In other words, it is preferable that in a case of instructing for a change in a position of one layer boundary toward a side of neighboring other layer boundary among the plurality of layer boundaries in the tomographic image, the positional relation between one and other layer boundaries in the depth direction of the tomographic image is not inverted. Namely, the vertically structural relationship thereof in the depth direction is maintained. In such case, it is further preferable that when one and other layer boundaries contact with another and the position of one layer boundary is additionally changed toward the other layer boundary side, the positions of one and other layer boundaries are changed at the same time while maintaining the condition where one and other layer boundaries contact with another. In addition, it is further preferable that after changing the position of one layer boundary with the position of other layer boundary at the same time, only the position of one layer boundary is changed to another side opposite to the side of other or neighboring layer boundary, the condition where one and other layer boundaries contacts with another is changed to a condition where one boundary becomes apart from the neighboring layer boundary, and the position of one layer boundary is changed to the another side opposite to the side of other or neighboring layer boundary.

FIG. 4E illustrates a result of the processing performed when the cursor 420 moves the control point downward. As illustrated in the figure, when the moved control point is brought into contact with another boundary line (line indicating the layer boundary other than the layer boundary whose position has been changed), if the movement continues in the direction for causing the intersection, the position of the other boundary line is also updated.

In addition, it is known that several layers of the retina are extremely thin in a central pit thereof anatomically. In this embodiment, it is assumed that the layer boundary lines between those converge to one point in the vicinity of the central pit. In addition, when the one point is moved, the positions of the other boundary lines converged to the one point are also updated. FIG. 4D illustrates a result of the processing.

<Step S335: Determine Whether or not to Cancel Update of Boundary Line>

In Step S335, the UI control unit 140 determines whether or not to cancel the update of (editing processing for) the boundary line. The UI control unit 140 displays a cancel button on the display unit 170, and the operation unit 130 determines based on the operation of the operator whether or not the mouse has clicked on the cancel button. When it is determined that the cancel button has been clicked on, the processing advances to Step S336. When it is determined that the cancel button has not been clicked on, the processing of Step S330 is brought to an end.

<Step S336: Cancel Update of Boundary Line>

In Step S336, work for canceling the update of (editing processing for) the boundary line is executed. To that end, the UI control unit 140 sends a canceling command to the layer boundary information updating unit 160, and the layer boundary information updating unit 160 acquires original information on the changed layer boundary line from the layer boundary information recording unit 120.

According to the above-mentioned configuration, in the editing of the position of the layer boundary line, by correcting the position of another layer boundary line to information on an anatomical basis, the position of the other boundary line is also corrected by editing one boundary line, which can reduce load on the operator. Alternatively, the layer boundary line is displayed on the tomographic image, the boundary line to be edited is highlighted, and the control points are displayed with overlaps, to thereby make it easier to recognize the position of the boundary line to be edited. Alternatively, in the moving of the position of the control point, by recalculating the position of the adjacent control point, the position of the same layer boundary line in the adjacent tomographic image is smoothed out, which produces an effect that the operator can efficiently and easily correct the position of the layer boundary line with a small number of operations.

Second embodiment: add attribute indicating edit status in part of layer boundary The first embodiment has described the example in which, in order to smooth out the change in the position of the layer boundary line in the adjacent tomographic image, the position of the control point on the layer boundary line is moved to correct the position of the control point or the position of the layer boundary line in the adjacent tomographic image. Described in this embodiment is a method of inhibiting the control point moved by the operator from having the position corrected by the interpolation or the like.

The image processing apparatus 10 according to this embodiment is the same as the first embodiment, and hence the description thereof is omitted. A procedure for processing according to this embodiment is the same as the processing procedure of the first embodiment except for Step S331, Step S332, and Step S333, and hence the description thereof is omitted. Here, Step S331, Step S332, and Step S333 that are executed in the second embodiment are set as Step S331B, Step S332B, and Step S333B, respectively.

<Step S331B>

In Step S331B, the UI control unit 140 displays the control point 410 on the layer boundary line to be edited, and inputs the operation of the operator received from the operation unit 130. In Step S331B of this embodiment, in addition to the processing of Step S331 of the first embodiment, the layer boundary information updating unit 160 attaches an "edit status" tag to each control point. The value of the "edit status" tag is set to "edited" or "unedited". In an initial state, the "edit status" tags of all the control points are set to "unedited". In other words, the layer boundary information updating unit 160 imparts an attribute indicating the edit status to the control point, and executes the changing of the information on the layer boundary line based on the attribute. Further, it is preferred that the display form indicating the attribute be displayed for each control point. This enables the examiner to confirm the edit status with ease.

<Step S332B>

In Step S332B, the layer boundary information updating unit 160 moves the selected control point. In Step S332B of this embodiment, in addition to the processing of Step S332 of the first embodiment, the layer boundary information updating unit 160 attaches the "edited" tag to each control point moved by inputting the operation of the operator.

<Step S333B>

In Step S333, the layer boundary information updating unit 160 recalculates the position of the layer boundary line and the position of another control point in accordance with the movement of the control point performed in Step S332. In Step S333B of this embodiment, in the same manner as the processing of Step S333 of the first embodiment, the interpolation is performed for the position of the boundary line between the control points. However, in a case where an "edited" tag is attached is to the control point, the control point is preferentially employed as a sample, and the control point to which an "edited" tag is attached is inhibited from being moved by the interpretation. In the same manner, the control point in the adjacent tomographic image is also employed as a sample for the interpolation when the "edited" tag is attached thereto, and is inhibited from being moved.

In the above-mentioned manner, a flow of the processing executed in this embodiment is brought to an end.

Note that, this embodiment has been described by taking the example in which the "edit status" tag is attached to the control point, but is not limited to the control point, and the same tag may be attached to all boundary points on the boundary line recorded by the layer boundary information recording unit 120. In this case, it is assumed that the layer boundary information recording unit 120 also records information on the "edit status" tag. In this case, in Step S334, the layer boundary information updating unit 160 updates the position of another boundary line to which the "unedited" tag is attached. Further, it is preferred to display a display form (other than the plurality of regions) that differs depending on the attribute in order to allow the specter to identify the attribute with ease.

With the above-mentioned configuration, the "edit status" tag is attached to the position of the control point that has once been corrected by the operator so as to inhibit the position of the "edited" control point from being corrected by the interpolation, which can prevent the position of the control point that has already been edited by the operator from being changed unintentionally by the interpolation or the like. Note that, in a case where there is no control point, it suffices that, when a part of the display form indicating the layer boundary is selected, the attribute indicating the edit status is added to the selected region.

Further, in the case where there is no control point, it is preferred that, when a part of the display form indicating the layer boundary is selected, the selected region be displayed in a display form different from another region. This allows, for example, the attribute to be identified with ease.

Third embodiment: edit layer boundary information on restructured tomographic image The first embodiment has described the method of displaying the layer boundary line in the tomographic image of the three-dimensional tomographic image formed of the plurality of two-dimensional tomographic images and allowing the operator to edit the layer boundary line in the tomographic image. Described in this embodiment is a method of editing the position of the layer boundary line in the tomographic image restructured from the three-dimensional tomographic image.

The image processing apparatus 10 according to this embodiment is the same as the first embodiment, and hence the description thereof is omitted. A procedure for processing according to this embodiment is the same as the processing procedure of the first embodiment except for Step S333, and hence the description thereof is omitted. Here, Step S333 that is executed in the third embodiment is set as Step S333C, respectively.

Figure 5A:
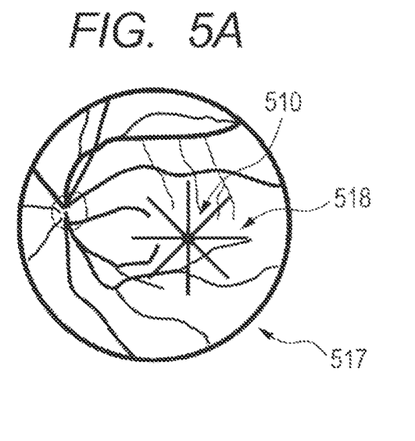
FIGS. 5A, 5B, 5C, 5D and 5E are diagrams illustrating processing results according to the example of the embodiment of the present invention.
Figure 5B:
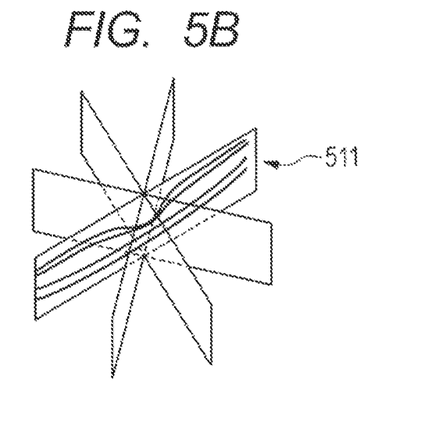
Figure 5C:
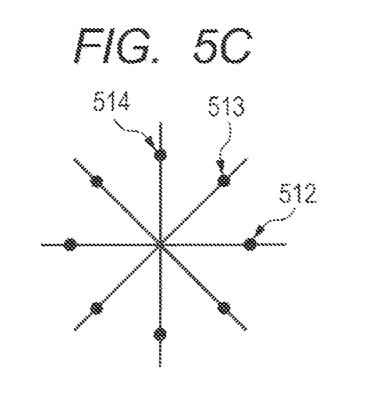

The tomographic image used for the description of this embodiment is a radial scan tomographic image. The radial scan tomographic image is a tomographic image photographed while subjecting the retina to a radial scan. The radial scan requires a central point on the retina and distance information on the scan of one tomographic image. FIGS. 5A to 5E illustrate examples of the tomographic image for the radial scan. Reference numeral 517 of FIG. 5A denotes a fundus image of the retina. Reference numeral 518 denotes a scanning position in the radial scan tomographic image. Reference numeral 510 denotes the central point of the radial scan. FIG. 5B illustrates an example of the tomographic image photographed by the radial scan. Reference numeral 511 denotes an example of one tomographic image. FIG. 5C illustrates the tomographic image obtained when viewed from a Z-axis direction. Reference numeral 512 denotes an example of one tomographic image. Reference numerals 513 and 514 denote the control points located on the same layer boundary line in the different tomographic images. Reference numerals 513 and 514 have the same distance from the center. Here, the radial scan tomographic image formed of four tomographic images is described as an example, but this embodiment is not limited to this number, and the number may be six or twelve.

<Step S333C>

In Step S333C, the layer boundary information updating unit 160 recalculates the position of the layer boundary line based on the control point moved in Step S332. In this embodiment, first, the position of the layer boundary line displayed in the same tomographic image is recalculated. In this embodiment, the interpolation of the position of the boundary line between the control points is the same as Step S333.

The interpolation for the boundary line between the boundary lines is also performed by using the control point on the layer boundary line in the tomographic image being edited within another tomographic image that forms the radial scan tomographic image. In this embodiment, the control point having the same distance from the center of the radial scan is subjected to the interpolation. In short, the calculation for the interpolation is performed by creating a one-dimensional list of the control points located on a concentric circle about the center of the radial scan. In other words, in a case where the tomographic image has been obtained by the radial scan, the layer boundary information updating unit 160 performs the interpolation for the layer boundary line based on the control points arranged on the concentric circle having the same center as the center of the radial scan.

However, the respective control points on the retina are already known, and hence it is conceivable to perform the calculation for the interpolation for the control point or the boundary line in a two-dimensional manner.

The other processing is the same as Step S333.

(Modified Example)

Note that, in this embodiment, the description has been made of the example of the tomographic image photographed by the radial scan, but the radial scan tomographic image may be restructured from 3-D tomographic image data performed in such parallel photographing as described in the first embodiment. In this case, in Step S210, the tomographic image acquiring unit 110 restructures the radial scan tomographic image, and further in Step S220, the UI control unit 140 acquires information on the layer boundary line corresponding to the A-scan unit of the restructured tomographic image from the layer boundary information recording unit 120, and displays the information on the layer boundary line so as to be overlapped with the radial scan tomographic image. After that, the image processing apparatus 10 of this embodiment performs the editing processing, and when the editing processing is finished, in Step S260, the layer boundary information updating unit 160 reflects the information on the layer boundary line edited from the radial scan tomographic image onto original 3-D tomographic image data.

Note that, this proposition is not limited to the interpolation performed on the radial scan tomographic image. For example, the control point on the radial scan may be moved by the operation of the operator, information on the movement of the control point may be reflected on an original 3-D tomographic image, and the interpolation may be performed on the 3-D tomographic image.

According to the above-mentioned configuration, it is possible to perform the interpolation for the position on the layer boundary line on the concentric circle in the case of the radial scan tomographic image. In addition, also in the case of the 3-D tomographic image photographed in parallel, the radial scan tomographic image can be restructured from the 3-D tomographic image, and the interpolation can be performed for the position of the layer boundary line, which enables the editing to be performed for the tomographic image that is familiar to the operator.

Fourth embodiment: edit layer boundary information on tomographic image of optic papilla portion In the first embodiment, the description has been made of the method of editing the layer boundary line in the tomographic image of the macula portion. In this embodiment, a description is made of a method of editing the layer boundary line in the tomographic image of a papilla portion.

Figure 5D:
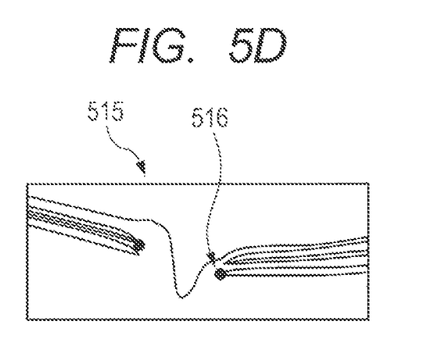

FIG. 5D illustrates an example of a papilla portion tomographic image 515. Illustrated in the papilla portion tomographic image 515 is an RPE edge point 516 being a point indicating the position of an RPE edge. The papilla portion tomographic image is displayed normally as the radial scan tomographic image with the papilla portion set as the center.

In this embodiment, the control point is placed at the RPE edge point. No limitation of the position of a movement destination of the control point at the RPE edge point is imposed on the operation of the operator as long as the control point falls within the same tomographic image. In the case of the radial scan tomographic image, an angle of the tomographic image is the positional information, and hence information on an angle of the control point is assumed to be unchanged.

The image processing apparatus 10 according to this embodiment is the same as the third embodiment, and hence the description thereof is omitted. A procedure for processing according to this embodiment is the same as the processing procedure of the first embodiment except for Step S333, and hence the description thereof is omitted. Here, Step S333 that is executed in the third embodiment is set as Step S333D, respectively.

<Step S333D>

In Step S333D, the layer boundary information updating unit 160 recalculates the position of the RPE edge point in accordance with the movement of the control point in Step S332. The interpolation for the position of the RPE edge point in the other tomographic image is performed by using the control point at the RPE edge point in the tomographic image being edited within another tomographic image that forms the radial scan tomographic image. In this embodiment, the fixed position of the RPE edge point is set as the angle. The distance from the radial scan and the position in the depth direction (Z-direction) are subjected to the interpolation.

In other words, in the case where the tomographic image has been obtained by the radial scan, the layer boundary information updating unit 160 performs the interpolation for the distance from the center of the radial scan for the RPE edge point in the eye to be inspected and the position in the depth direction of the tomographic image.

$$R(a)=\text{Int}R(a) \tag{2}$$

$$Pz(a)=\text{Int}P(a) \tag{3}$$

where R(a) represents the position from the center of the radial scan of the RPE edge point in an angle "a" direction. IntR(a) represents the position in the depth direction (Z-direction) of the RPE edge point in the angle "a" direction.

Figure 5E:
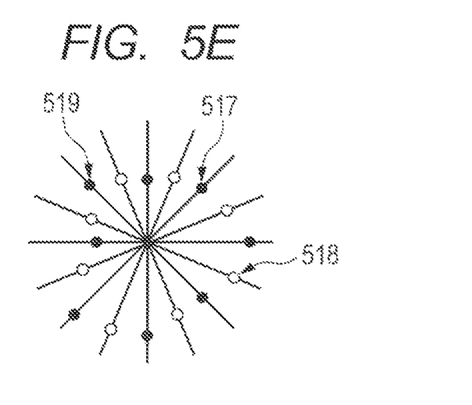

FIG. 5E illustrates a processing result from the image processing apparatus 10 according this embodiment. FIG. 5E illustrates the radial scan tomographic image of the papilla portion obtained when viewed from the Z-axis direction. Reference numeral 517 denotes the control point at the RPE edge point which has been edited by inputting the operation of the operator. Reference numeral 518 denotes the RPE edge point whose distance from the center and position in the depth direction (Z-direction) have been corrected in the interpolation. Reference numeral 519 denotes one tomographic image of a papilla portion radial scan tomographic image. In other words, in this embodiment, the tomographic image acquiring means restructures the radial scan tomographic image from the tomographic image, and the layer boundary information recording unit 120 changes the recorded information on the layer boundary line based on the information on the layer boundary line changed to the radial scan tomographic image or the information on the position of the RPE edge.

According to the above-mentioned configuration, the position (distance from the center of the radial scan and a position in the depth direction) of the RPE edge point can be corrected in a case of the papilla portion radial scan tomographic image, which facilitates the editing of the RPE edge.

(Other Embodiments)

Further, the object of the present invention is achieved also by supplying the apparatus or system with a recording medium having recorded thereon a program code of software for realizing the functions of the above-mentioned embodiments and by causing a processor of the apparatus or system to execute the program code stored in the recording medium.

In this case, the program code itself, which is read from the recording medium, realizes the functions of the above-mentioned embodiments, and the recording medium having recorded thereon the program code constitutes the present invention.

Further, a case where, by executing the program code read by the computer, an operating system (OS) or the like running on the computer performs a part or all of actual processing and the functions of the above-mentioned embodiments are realized by the processing is included.

In addition, a case where the program code read from the recording medium is written to a memory within a function expansion card or function expansion unit included within the computer, a processor within the expansion card or expansion unit performs a part or all of actual processing, and the functions of the above-mentioned embodiments are realized by the processing is included.

In a case where the present invention is applied to the above-mentioned recording medium, the recording medium stores the program code corresponding to the figures illustrated above.

Note that, the above description of the embodiments is an example of a preferred image processing apparatus according to the present invention, and the present invention is not limited thereto.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-190610, filed Aug. 30, 2012, which is hereby incorporated by reference herein in its entirety.

What is claimed is:

1. An image processing apparatus, comprising:
a display control unit for causing a display unit to display respective display forms indicating a plurality of layer boundaries in positions corresponding to the plurality of layer boundaries of a tomographic image of a retina in an overlapped state;
an instruction unit for providing an instruction for changing at least one of positions of the display forms overlapped on the tomographic image; and
a changing unit for changing, when the changing unit is instructed by the instruction unit (a) to come into contact with two adjacent display forms of the display forms indicating the plurality of layer boundaries and (b) to change the position of one of the two adjacent display forms toward a side of another display form, the positions of the two adjacent display forms in conjunction with each other.

2. The image processing apparatus according to claim 1, wherein the display form instructed attaches an attribute indicating an edit state different from the other display forms to the selected display form.

3. The image processing apparatus according to claim 1, wherein the display control unit causes, when each of the display forms indicating the plurality of layer boundaries is instructed by the instruction unit, the display unit to display the instructed display form in a display form different from other display forms.

4. The image processing apparatus according to claim 1, wherein the changing unit changes, when the changing unit is instructed by the instruction unit (a) to come into contact with two adjacent display forms and (b) to change the position of one of the two adjacent display forms toward the side of another display form, the positions of the two adjacent display forms in conjunction with each other so as to maintain a positional relationship between the two adjacent display forms and so as not to intersect with each other.

5. The image processing apparatus according to claim 1, wherein the changing unit performs, based on the changed position, interpolation with respect to the position of the region other than the plurality of regions on the display forms indicating the plurality of layer boundaries.

6. The image processing apparatus according to claim 5, wherein the changing unit performs, in a case where the tomographic image has been obtained by radial scan, the interpolation based on a plurality of regions arranged on a concentric circle having a center corresponding to a center of the radial scan.

7. The image processing apparatus according to claim 1, further comprising a unit for restructuring a radial scan tomographic image from the tomographic image,
wherein the changing unit changes the information on the position of the layer boundary based on information on the layer boundary changed to the radial scan tomographic image or information on a position of an RPE edge.

8. The image processing apparatus according to claim 1, wherein the changing unit changes, in a case that the instruction unit provides an instruction for changing a position of a first layer boundary among the plurality of layer boundaries to a side of a second layer boundary among the plurality of the layer boundaries, which neighbors the first layer boundary, the position of the first layer boundary and the second layer boundary so as not to invert a positional relationship between the first layer boundary and the second layer boundary in a depth direction of the tomographic image.

9. The image processing apparatus according to claim 8, wherein the changing unit changes, in a case that the first layer boundary contacts the second layer boundary and the position of the first layer boundary additionally changes to the side of the second layer boundary, the positions of the first layer boundary and the second layer boundary while maintaining the condition where the first layer boundary contacts the second layer boundary.

10. The image processing apparatus according to claim 9, wherein the changing unit changes, in a case that after changing the position of the first layer boundary with the position of the second layer boundary the position of the first layer boundary is changed to another side opposite to the side of the second layer boundary, the condition where the first layer boundary contacts the second layer boundary to a condition where the first layer boundary becomes apart from the second layer boundary, and changes the position of the first layer boundary to the another side.

11. An image processing method, comprising:
causing a display unit to display respective display forms indicating a plurality of layer boundaries in positions corresponding to the plurality of layer boundaries of a tomographic image of a retina in an overlapped state;
providing, by an instruction unit, an instruction for changing at least one of positions of the display forms overlapped on the tomographic image; and
changing, when instructed by the instruction unit (a) to come into contact with two adjacent display forms of the display forms indicating the plurality of layer boundaries and (b) to change a position of one of the two adjacent display forms toward a side of another display form, the positions of the two adjacent display forms in conjunction with each other.

12. A non-transitory computer-readable storage medium having recorded thereon a program for causing a computer to execute the image processing method according to claim 11.

13. An image processing method according to claim 11, wherein in the changing, in a case that the instruction unit provides an instruction for changing the position of the first layer boundary among the plurality of layer boundaries to a side of a second layer boundary among the plurality of the layer boundaries, which neighbors the first layer boundary, the position of the first layer boundary and the second layer boundary is changed so as not to invert a positional relationship between the first layer boundary and the second layer boundary in a depth direction of the tomographic image.

14. A non-transitory computer-readable storage medium having recorded thereon a program for causing a computer to execute the image processing method according to claim 13.

15. The image processing method according to claim 11, wherein, when instructed by the instruction unit (a) to come into contact with the two adjacent display forms and (b) to change the position of one of the two adjacent display forms toward the side of another display form, the positions of the two adjacent display forms are changed in conjunction with each other so as to maintain a positional relationship between the two adjacent display forms and so as not to intersect with each other.

* * * * *